United States Patent [19]
Nishihara

[11] Patent Number: 5,584,693
[45] Date of Patent: Dec. 17, 1996

[54] ARTIFICIAL DENTAL ROOT

[75] Inventor: Katsunari Nishihara, Tokyo, Japan

[73] Assignees: Katsunari Nishihara; Toyama Precious Metals Co., Ltd., both of Tokyo, Japan

[21] Appl. No.: 308,593

[22] Filed: Sep. 19, 1994

[30]     Foreign Application Priority Data

Feb. 7, 1994   [JP]   Japan .................................... 6-013503

[51] Int. Cl.$^6$ ............................ A61C 13/28; A61C 8/00; A61C 13/12; A61C 13/225
[52] U.S. Cl. ........................... 433/169; 433/173; 433/177; 433/201.1
[58] Field of Search ..................... 433/169, 172, 433/173, 174, 175, 176, 177, 220, 221, 224, 201.1

[56]                References Cited

U.S. PATENT DOCUMENTS

| | | | |
|---|---|---|---|
| 3,827,145 | 8/1974 | Richards | 433/175 |
| 4,195,409 | 4/1980 | Child | 433/175 |
| 4,324,550 | 4/1982 | Reuther et al. | 433/169 X |
| 5,074,792 | 12/1991 | Bernadat | 433/224 X |
| 5,174,755 | 12/1992 | Fukuda | 433/169 X |
| 5,362,234 | 11/1994 | Salazar et al. | 433/169 |

OTHER PUBLICATIONS

Oral Implantology And Biomaterials; Basic and Clinical Evaluation of Zirconia Ceramic Dental Implant System; pp. 83–91, 1989.

Oral Implantology And Biomaterials; Clinical Application of Dental Root Implant Using Bioactive Glass; pp. 145–149, 1989.

*Primary Examiner*—Nicholas D. Lucchesi
*Attorney, Agent, or Firm*—Flynn, Thiel, Boutell & Tanis, P.C.

[57]            ABSTRACT

An artificial tooth root undergoing connective tissue fusion when implanted. The artificial tooth root is columnar-shaped and has a crown (5) at its one end and an apex (6) at its other end. The artificial tooth root has a dual structure consisting of an outer root (7) and an inner root (8). The outer root (7) and the inner rook (8) have axially extending protrusions 4,4' and recesses 3,3' on their lateral sides and are affixed to each other by a resin adhesive (9).

11 Claims, 15 Drawing Sheets

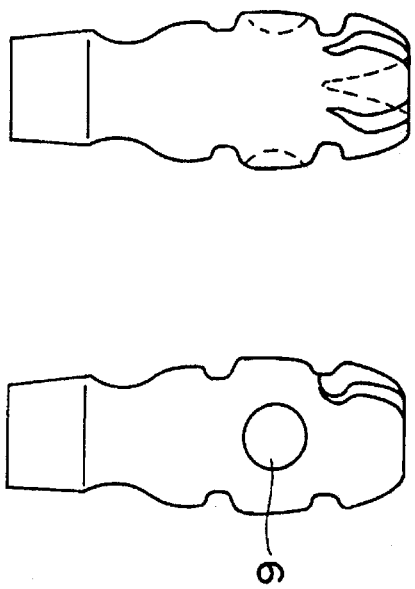
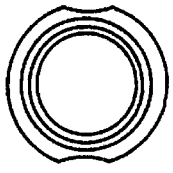
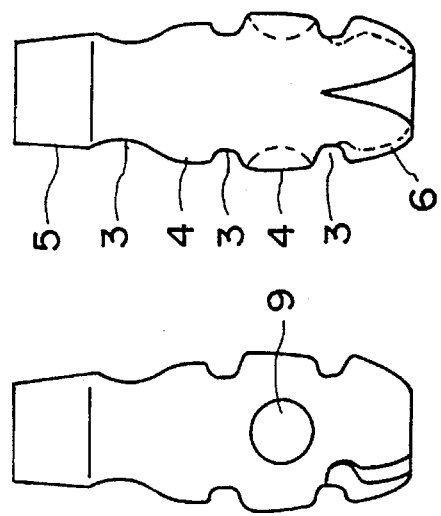
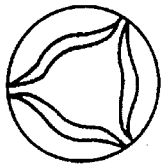
FIG. 9(a) FIG. 9(b) FIG. 9(c) FIG. 9(d) FIG. 9(e) FIG. 9(f)

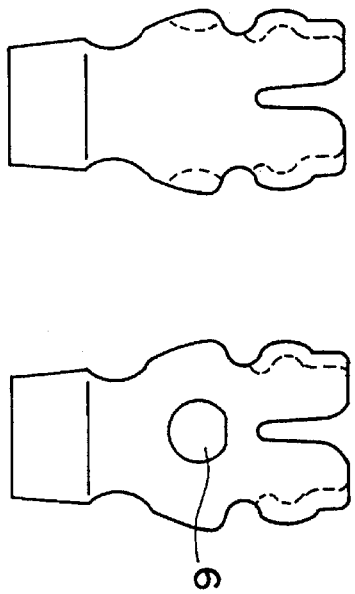
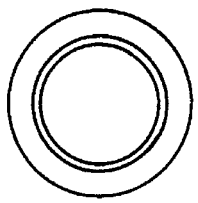
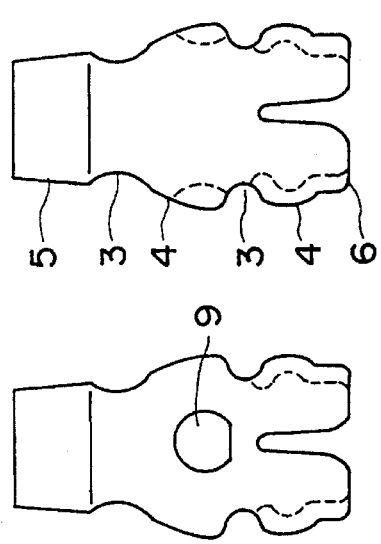
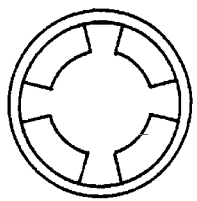
FIG.12(e) FIG.12(a) FIG.12(b) FIG.12(c) FIG.12(d) FIG.12(f)

ARTIFICIAL DENTAL ROOT

BACKGROUND OF THE INVENTION

1. Field of the Invention

This invention relates to an ankylosis type artificial tooth root of a dual structure in which the function of a periodontal membrane (periodontal ligament) is assumed by a buffer material.

2. Description of the Prior Art

It has long been practiced to have a device implanted directly in a jaw bone, in place of a denture, as a dental implant in order to replace a lost tooth. However, there is much to be desired in technical aspects and in respect of characteristics of the implant material.

For example, an artificial tooth root of bioactive ceramics or titanium in current use is not provided with an effective shock-absorbing or buffering mechanism because its connection with the jaw bone is via ankylosis or osseointegration. However, an ankylosis type tooth is found only in lower animals, such as reptiles, and not in higher animals. Therefore, an effective shock-absorbing mechanism needs to be devised in order to utilize it for a human.

That is, teeth of a mammal are required to have minor mobility in order to accommodate chewing, i.e, mastication. Thus the teeth of a mammal is connected by gomphosis to a jaw bone. On the other hand, ankylosis type teeth are characteristic of a reptile which cannot chew, and are necessarily fractured, so that, with certain reptiles, teeth are renewed 20 to 30 times. As a matter of fact, an artificial tooth root of a man, affixed to bone, is broken in many cases, if the tooth root is formed of ceramics. With an implant of a time-honored shape, a fibrous tissue having a function similar to the periodontal membrane is not produced because of its inadequate shape, even although it is made of a metallic material. As a result, the tooth root is occasionally fractured and, in a majority of cases, the bone tissue around the root is also broken.

The present invention provides an ankylosis type artificial tooth root in which the function of the periodontal membrane is taken over by a dual structure buffer material. The buffer material functions as transforming means for the principal stress trajectory, while the outer root of the artificial tooth root is equivalent to an alveolar bone formed around the inherent tooth root. In this manner, stable renewal and remodeling of bone around the artificial tooth root may be maintained for a prolonged time under maintenance of the chewing function.

SUMMARY OF THE INVENTION

For developing an artificial organ, such as an artificial tooth root, investigations into the shape and the function thereof are necessitated in addition to investigations into materials.

Thus the present invention provides a columnar-shaped artificial tooth root having a crown at one end and an apex at its other end, wherein the artificial tooth root has a dual structure comprising an outer root and an inner root, the lateral surfaces of the outer root and the inner root have axially extending alternate protrusions and recesses, the outer root is secured to the inner root by a buffer material, and wherein the apex end is round for an incisor, a premolar and a cuspid and is branched and recessed at the center for a molar.

With the present artificial tooth root, the Myses equivalent stress distributed in surrounding bone is significantly even distributed such that outstanding bone growth is produced in a range of distribution amounting to one-hundredth to one-tenth of the maximum stress value and ten times to tens of times of the minimum stress value. This is possibly ascribable to the piezoelectric current, streaming potential and to the fluidity of bone forming factors.

While investigations into the reaction of the material with the living body were conducted in the past, investigations into the reaction with the living body of artificial tooth roots of variable contours and into the shape effect by finite element analysis (FEA) have been conducted for realization of the present invention.

When implanting the artificial tooth root, the principal stress trajectory lines associated with the shape of the tooth roots are distributed around the artificial tooth root. Bone formation occurs along the locus of the principal stress trajectory line.

The tooth of the ankylosis system is totally different in the function from the tooth of the fibrous connective tissue system. With the tooth fused to bone, the principal stress trajectory passed through the tooth root and directly flows as a continuum through bone.

That is, the jaw bone and the tooth together cope with the biting force. However, since the bone and the artificial tooth root differ significantly in the Young's modulus or Poisson's ratio, bone and the tooth root are fused together under no load or under a small load, while interfacial separation necessarily incurs on reiteration of larger loads. This has been found by calculations thirty years ago in connection with the strength of the materials. Thus, it has been known that, even with a strength equal to three times the theoretical destruction strength, separation or destruction is necessary incurred under a load if a rigid body is connected to a rigid system. However, this is scarcely taken into account nowadays in the field of medicine and dentistry. It is noted that a strength equal to the theoretical destruction strength cannot be realized.

On the contrary, analyses of the distribution of the principal stress trajectory for the artificial tooth root of the fibrous connective tissue affixture type have revealed that the stress is first carried by the tooth root such that the principal stress trajectory line is converted by the fibrous tissue around the tooth into parallel and orthogonal components which are clearly demarcated from each other in plane strain state. It is a crucial finding that, while there are only two types of principal stress trajectories, as in the case of electromagnetic waves, the periodontal ligament represents the converting mechanism for the principal stress trajectory. Those running in parallel and orthogonally make up the alveolar bone and the bone trabeculae, respectively. The principal stress trajectory passing through the alveolar bone orient to and terminate at the cortical bone of the jaw bone, while the principal stress trajectory line passing orthogonally, through the bone trabeculae affixed to the alveolar bone likewise reaches and terminates at the cortical bone of the jaw bone. That is, the biting force applied to the teeth is taken charge of in its entirely by the cortical bone of the jaw bone. Thus the tooth and the jaw bone of higher animals may be said to be an unprecedented highly specialized mechanical functional system. With the artificial tooth root of the present invention, the mechanism of the periodontal fibrous tissue, which should substitute for the periodontal ligament, is accomplished by a buffer material present in the gap of the dual structure. An outer root corresponds to the alveolar bone and is fused by ankylosis to the surrounding bone. Since the principal stress trajectory is already transformed by the buffer material and thereby equalized, an extremely small load is applied in the fused zone of the outer root and bone, as a result of which, the artificial tooth root can withstand prolonged use similarly to the natural tooth root, in order to maintain bone remodeling.

With the artificial tooth root of the present invention, the inner surface of the outer root may be of a simple cylindrical shape or of an undulating shape.

BRIEF DESCRIPTION OF THE DRAWINGS

FIGS. 9a to 9f are schematic views showing an example of an artificial tooth root for a molar for an upper jaw.

FIGS. 12a to 12f are schematic views showing still another example, of an artificial tooth root for a molar for a lower jaw.

DETAILED DESCRIPTION OF THE PREFERRED EMBODIMENTS

The operation of the artificial tooth root according to the present invention is hereinafter explained in connection with the shape of an artificial tooth root of the present invention.

Figure 1:
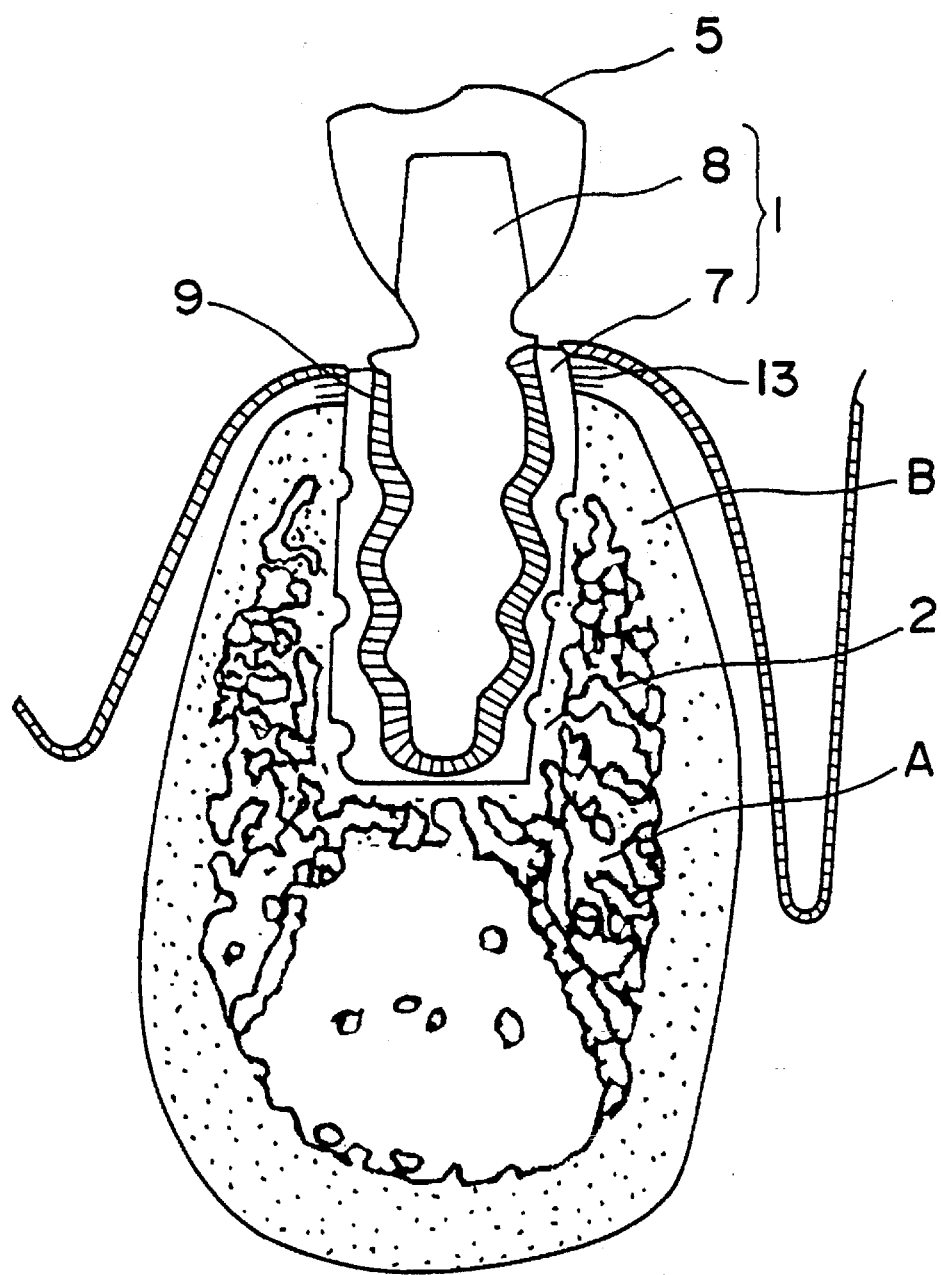
FIG. 1 is a schematic side view illustrating the operation of an artificial tooth root according the present invention.
Figure 2:
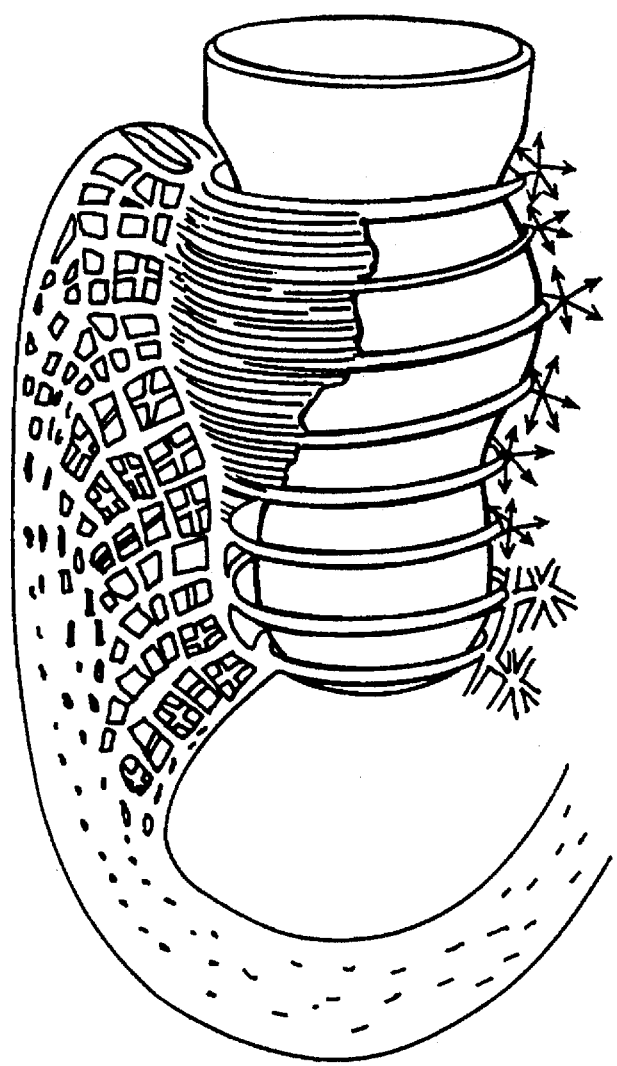
FIG. 2 is a perspective view showing the remodeling of a bone tissue of a periodontal area coincident with the principal stress trajectory line in a natural tooth and an artificial tooth of a connective tissue affixture type.

FIG. 1 schematically shows the relation of ankylosis between an artificial tooth root 1 of the present invention and a bone tissue 2 around the tooth root 1. The bone tissue 2 is formed around an outer root 7 of the artificial tooth root 1 of the present invention. In a submuscosal tissue directly below an epithelial attachment, a fibrous tissue 13 runs orthogonally so as to be affixed to the outer root 7. A tooth crown 5 and an inner tooth root 8 are affixed to the outer root 7 via a buffer material 9. A bone rib A is connected to an alveolar bone derived from the artificial tooth root. A cortical bone B defines the contour line of the jaw bone.

Figure 3:
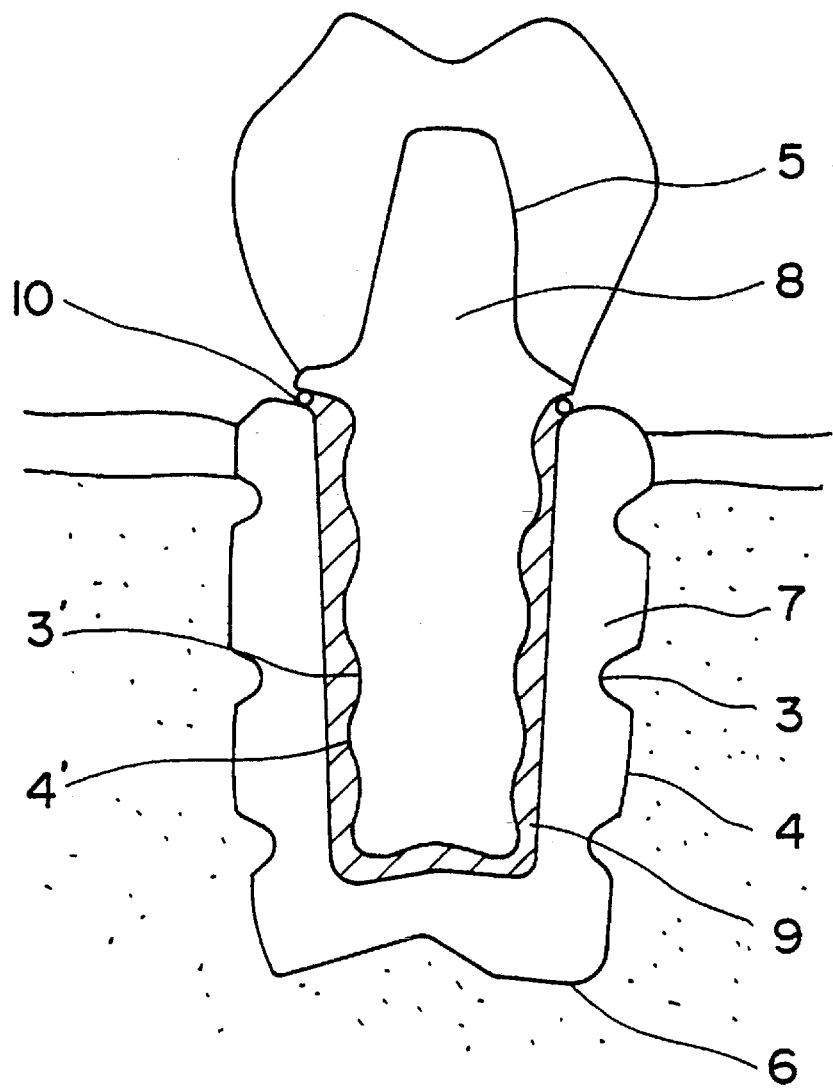
FIG. 3 is a schematic view showing an artificial tooth root according to the present invention.
Figure 4:
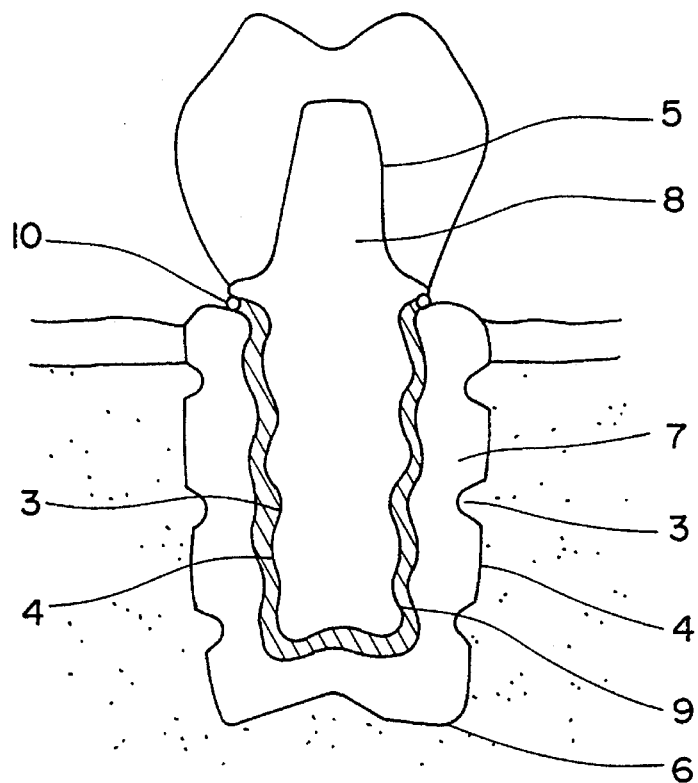
FIG. 4 is a schematic view showing a modification of an artificial tooth root according to the present invention.

The artificial tooth root according to the present invention is shown in cross-sectional views in FIGS. 3 and 4. The artificial tooth root of the present invention is made up of the outer root 7 and the inner tooth root 8 secured to the inside of the outer root 7 via the buffer material 9, such as a resin adhesive. The lateral side of the outer root 7 is formed with alternate axially extending protrusions 4 and recesses 3. Similarly, the lateral side of the inner tooth root 8 is formed with alternate protrusions 4' and recesses 3'. Both of the lateral sides are undulating in contour. The buffer material 9, such as a resin adhesive, is providing a space between the outer root 7 and the inner tooth root 8 for bonding them together. During charging of the resin adhesive 9, a ball-shaped stop 10 formed of plastics may be arranged, if so desired, in order to secure the outer root 7 and the inner root 8 easily and completely. The expression "axially" or "axial direction" herein refers to a straight line interconnecting the crown 5 and the apex 6. In FIG. 3, the inner surface of the outer root is simply cylindrical in contour, whereas, in FIG. 4, the inner surface of the outer root is undulating in profile.

Since the lateral surface of the outer root is undulating in profile, that is it has alternate protrusions and recesses, the outer root is of such a structure and shape that it may be readily fused to the surrounding bone. The inner tooth root is of a distributed stress shape as obtained by finite element analysis, and is of such a shape as will permit a principal stress trajectory line to be separated into two mutually perpendicular components.

The outer root and the inner root are bonded together by a resin adhesive for transforming the principal stress trajectory line. In addition, the adhesive layer acts as a cushion in order to eliminate the tendency for the biting force to destroy the bone.

Figure 5:
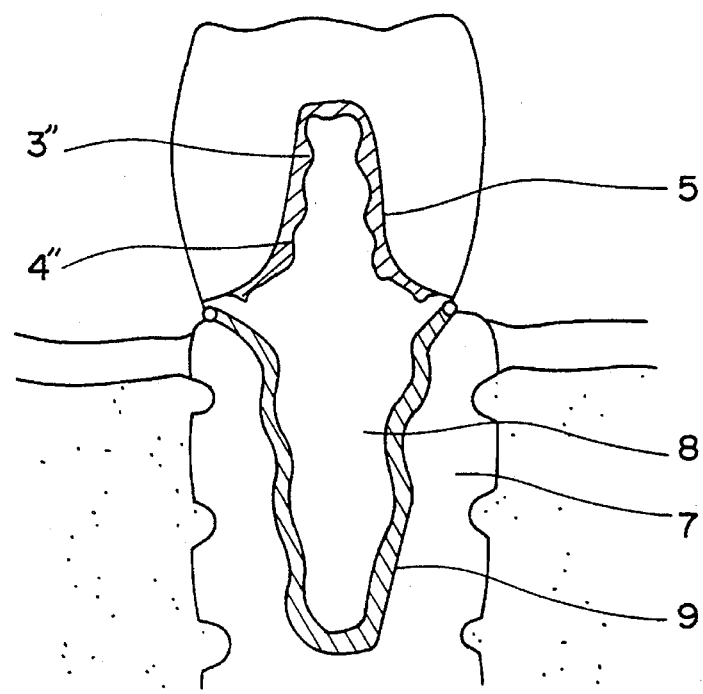
FIG. 5 is a schematic view showing another modification of an artificial tooth root according to the present invention.
Figures 6C, 6D:
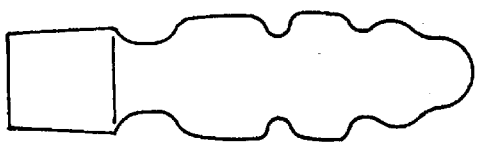
FIGS. 6a to 6f are schematic views showing an artificial tooth for an incisor for an upper jaw.
Figure 6E:
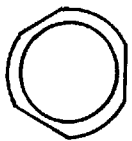
Figure 6A:
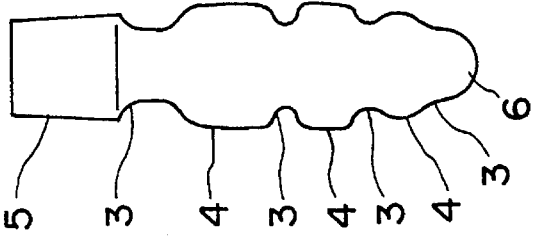
Figure 6F:
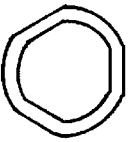
Figure 6B:
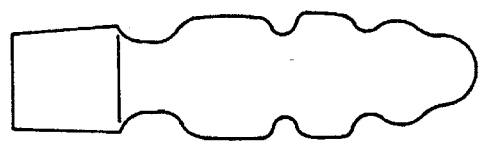
Figures 7C, 7D:
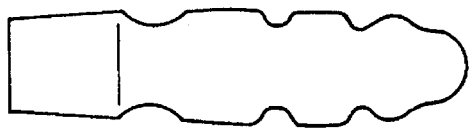
FIGS. 7a to 7f are schematic views showing an artificial tooth root for an incisor for a lower jaw and a cuspid.
Figure 7E:
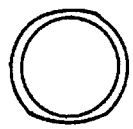
Figure 7A:
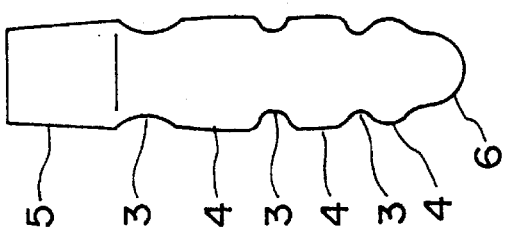
Figure 7F:
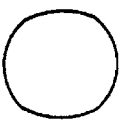
Figure 7B:
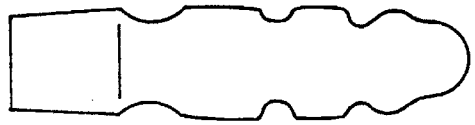
Figure 8D:
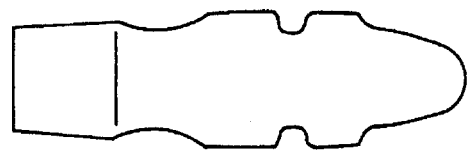
FIGS. 8a to 8f are schematic views showing an artificial tooth for a premolar for an upper jaw or a lower jaw.
Figure 8C:
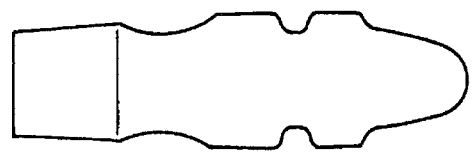
Figure 8E:
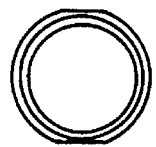
Figure 8A:
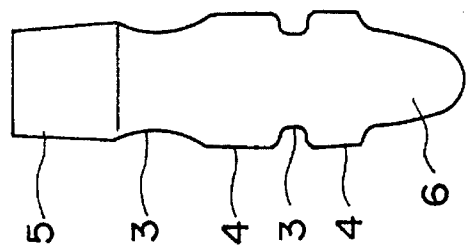
Figure 8F:
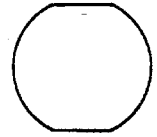
Figure 8B:
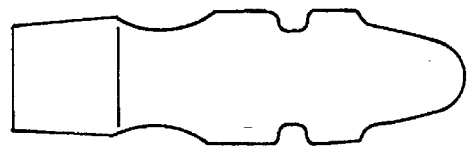
Figure 10D:
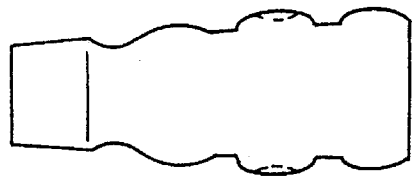
FIGS. 10a to 10f are schematic views showing an example of an artificial tooth root for a molar for a lower jaw.
Figure 10C:
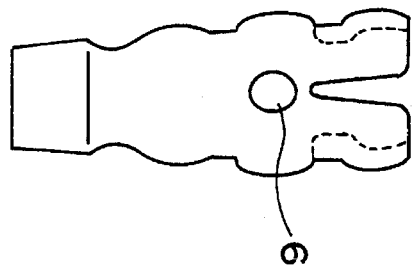
Figure 10F:
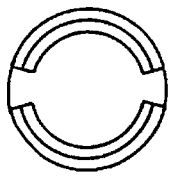
Figures 10A, 10B:
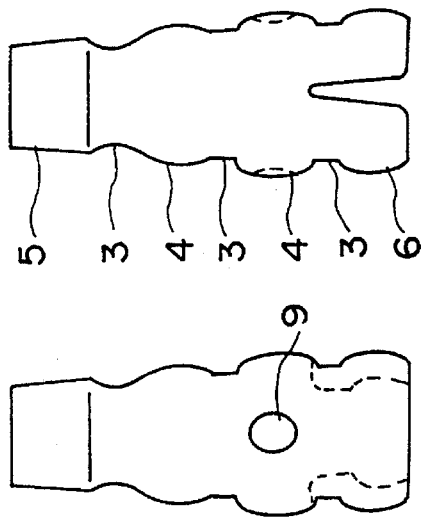
Figure 10E:
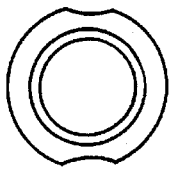
Figure 11D:
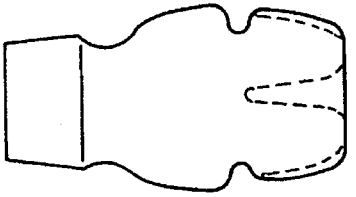
FIGS. 11a to 11f are schematic views showing another example of an artificial tooth root for a molar for an upper jaw.
Figure 11C:
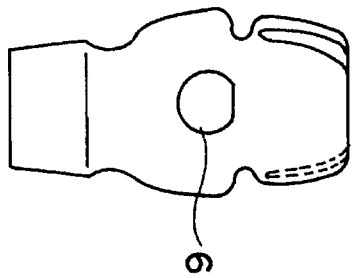
Figure 11A:
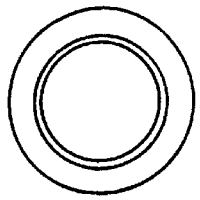
Figure 11B:
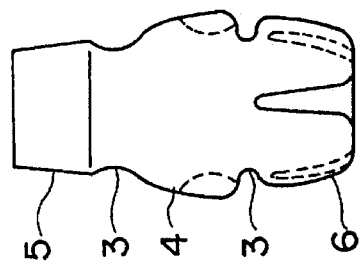
Figure 11E:
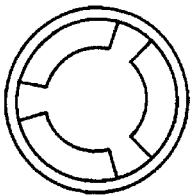
Figure 11F:
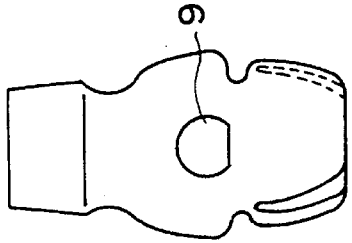

In an embodiment of the present invention, shown in FIG. 5, protrusions 4" and recesses 3" are alternately formed on the surface of the tooth crown 5. With the surface of the tooth crown 5 being of an undulating contour, not only can the tooth crown be secured in position using the buffer material, but also the adhesive layer acts as a cushion and as a principal stress trajectory line transforming means for eliminating the tendency for the biting force to destroy the inner root.

The outer root and the inner root differ in shape slightly depending on the setting sites. Thus, as shown in the following embodiments, the end of the apex is circular with the premolar or the cuspid, while it is branched and presents a central recess with the molar.

The material for the outer root is selected from the group consisting of metal, metal alloy, bioactive or non-bioactive ceramics, evaporated on or melded to metal, metal cermet presenting a metal or ceramic porous body, bioglass, and a composite material thereof.

The material for the inner root is selected from the group consisting of metal, metal alloy, ceramics, cermet's bioglass, plastics and composite materials thereof.

The buffer material may be an adhesive of plastics, cementing materials or metal (amalgam), such as, for example, "Super-Bond" (trade name), "Enginol Cement" (trade name) or amalgam.

The metals suitable as the material for the artificial tooth root of the present invention are hereinafter explained.

(i) Summary

Pure Ti or Ti alloys are tentatively applied in a wide field of application, such as in medicine or dentistry, as metal materials for living bodies. Above all, pure Ti is highly valued as an artificial tooth root inserted into the body because of its extremely low harmfulness to and improved affinity with the human body.

Investigations are also currently conducted for utilizing Ti-based shape memory alloys as an artificial root by taking advantage of the merit of their shape memory effect in immobilizing the tooth root after its insertion. Of these, the TiPd based shape memory alloy employed in dentistry, is mainly composed of Ti and Pd and is excellent in corrosion resistance, such that it is expected to be used as a material for an artificial tooth root which is particularly harmless to the living body.

(ii) Composition of TiPd-Co alloy

Figure 13:
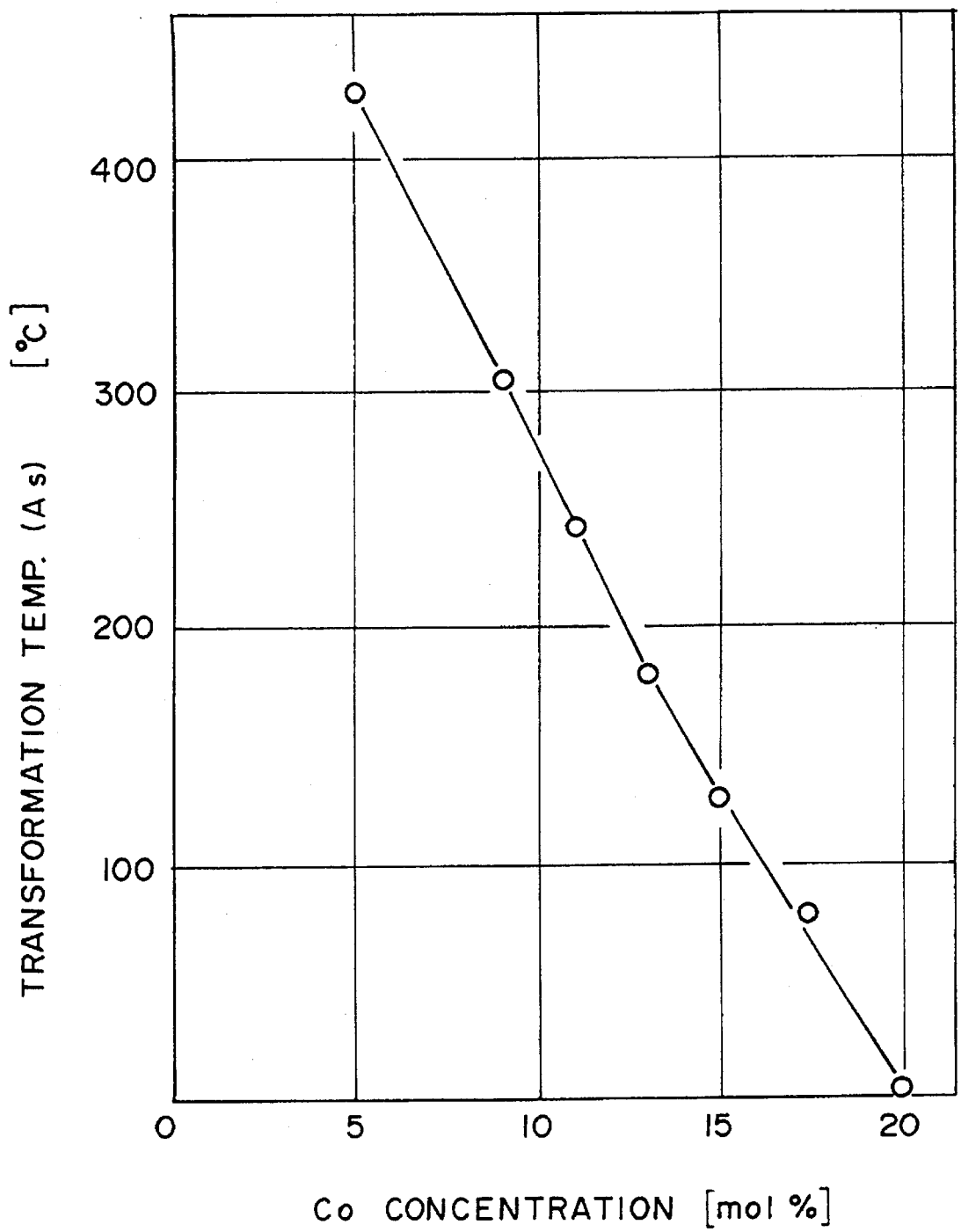
FIG. 13 is a graph showing the relation between the transformation temperature of a TiPd-Co alloy and the Co concentration.

The alloy has a composition in which Co is substituted for 19 to 20 mol percent of Pd of a Ti-50 mol % Pd alloy, and undergoes thermo-elastic martensitic transformation within a temperature range of 4° to 50° C. As shown in FIG. 13, as the Co concentration becomes higher, the transformation temperature is lowered, such that a composition having the Co concentration of 20 mol % undergoes transformation at 4° C.

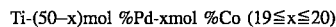

Ti-(50−x)mol %Pd-xmol %Co (19≦x≦20)

(iii) Corrosion Resistance

Figure 14:
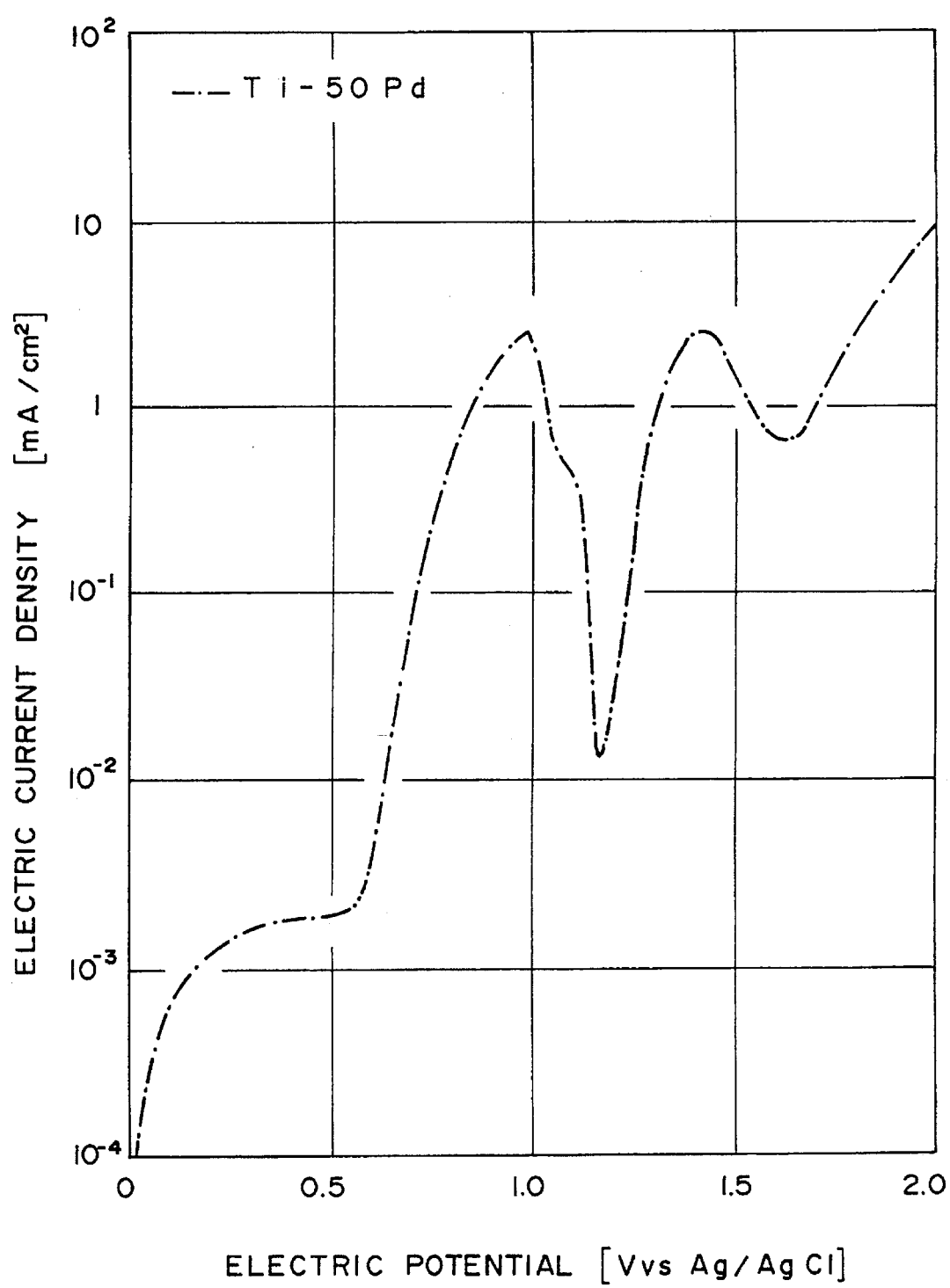
FIG. 14 is a graph showing an anodic polarization curve for a Ti-Pd alloy.
Figure 15:
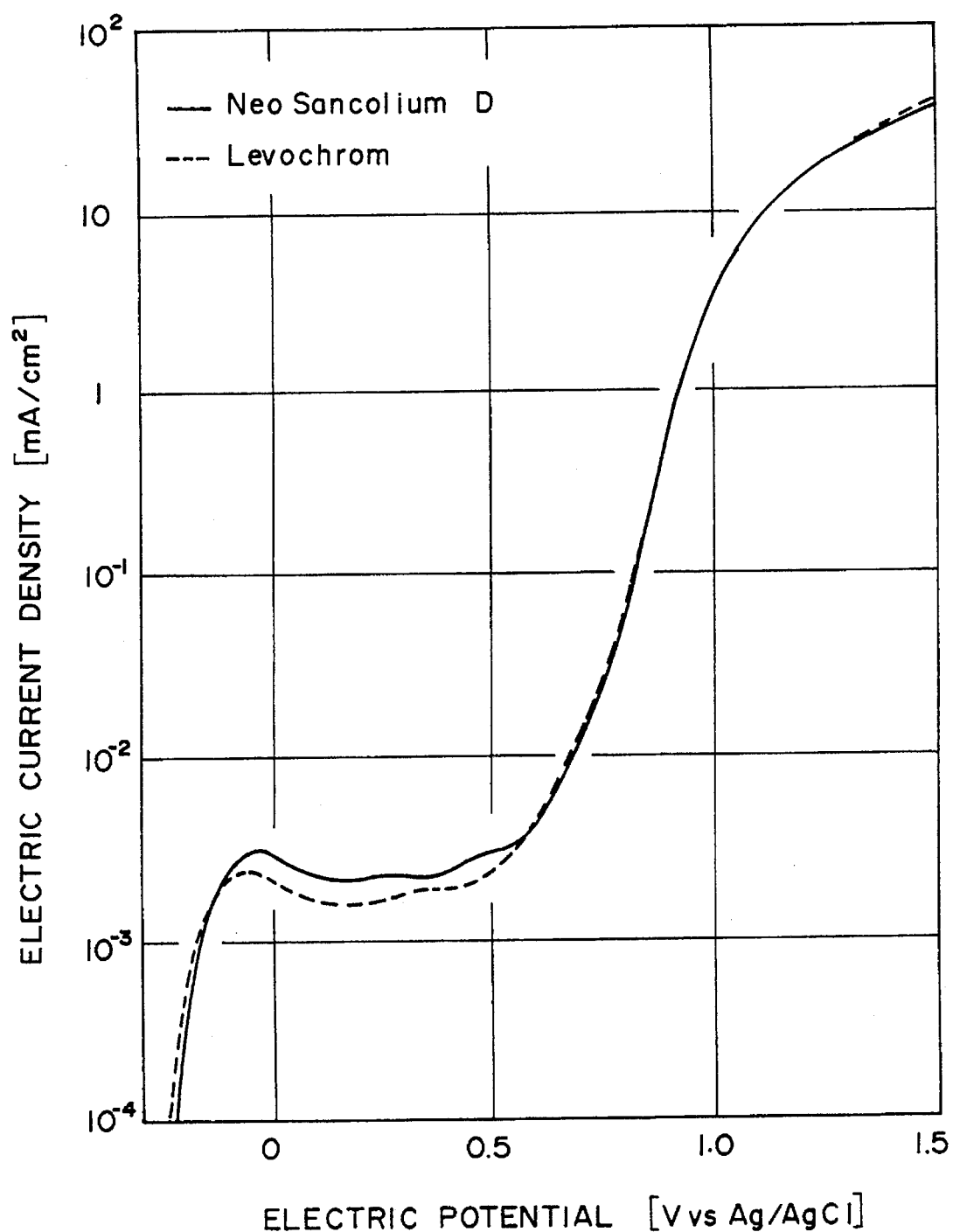
FIG. 15 is a graph showing an anodic polarization curve for a commercial Co-Cr alloy.
Figure 16:
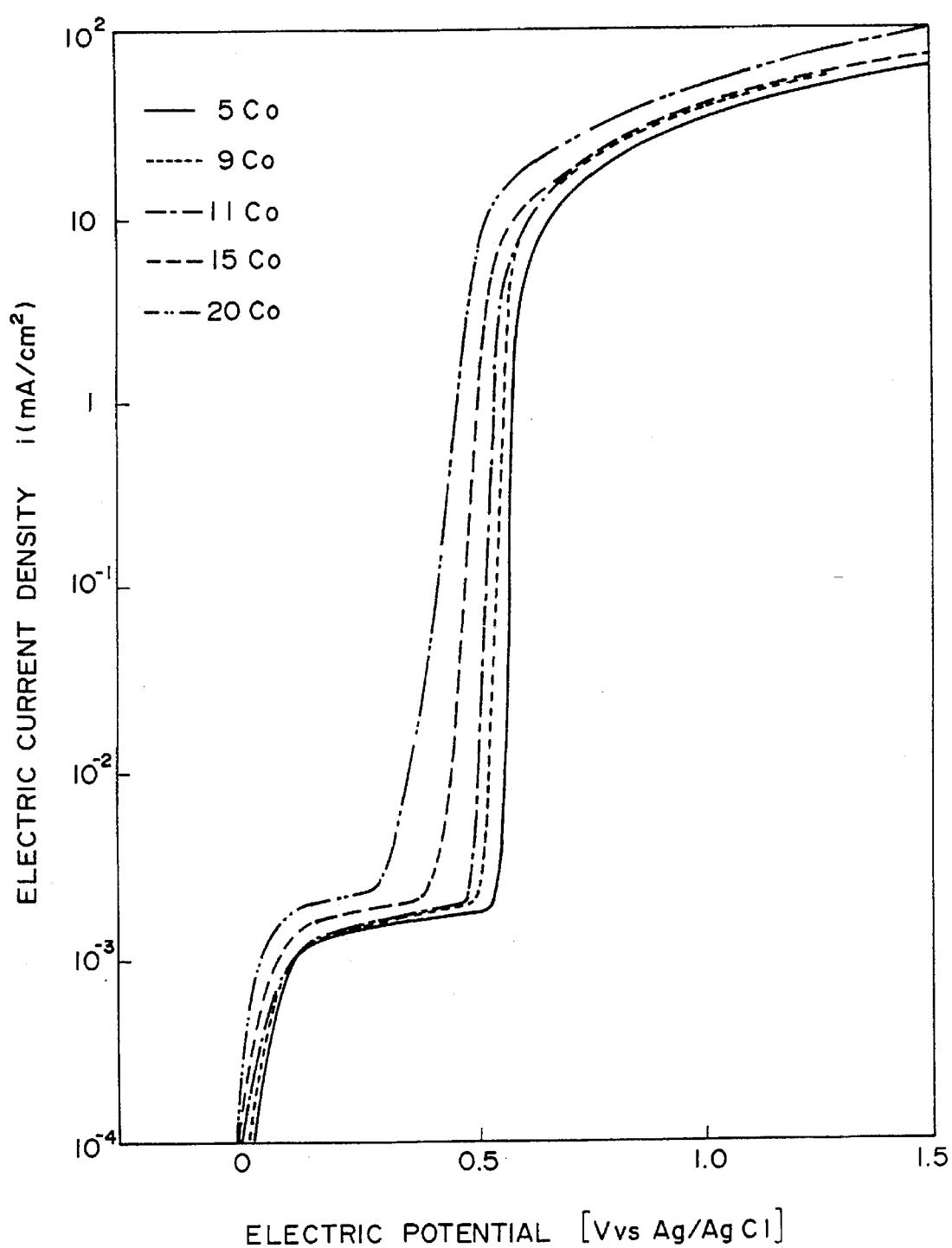
FIG. 16 is a graph showing an anodic polarization curve for a TiPd alloy.

Measurement of the anodic polarization of a Ti-50 mol % Pd alloy has revealed that, as shown in FIG. 14, an inactivated skin film is destroyed in the vicinity of a potential of 0.6 V. The alloy is thought to exhibit corrosion resistance comparable to that of a commercially available Co-Cr casting alloy. However, considering that the alloy has a higher self potential and a low current density in an inactivated zone due to generation of an inactivated skin film, the alloy is thought to exhibit corrosion resistance substantially equivalent to that of stainless steel SUS 304, even with a composition having a 20 mol % Co concentration.

(iv) mechanical properties

The TiPd-Co alloy has a micro-Vickers hardness on the order of 200, which is slightly less than the value of an aged type 10 alloy within the range of shape memory deformation. Although the alloy tends to crack and can be cold-worked only difficultly because of the smaller amount of plastic deformation caused by slip, it can be rolled easily if hot-worked at 800° to 900°. The shape memory effect is displayed if the Ti-30 mol % Pd-20 mol % Co alloy, subjected to bending deformation in the vicinity of 0° C. is heated to 26° C.

Ceramic materials are generally hydrophilic and compatible with the human body, so that they are suited for use in the present invention. Above all, the materials termed bioceramics are suitable for use in the present invention. Preferred specific examples of the ceramics include bio-inert alumina and zirconia, which hardly react with living bodies, and bio-active $3CaO.P_2O_5$ porous material, apatite hydroxide or apite-containing crystal glass, react with human bodies.

As plastic materials, those having a certain strength and expansion rate are preferred. Particularly preferred are so-called engineering plastics known as polyacetal resin, ABS resin, epoxy resin, polyamide resin, ionomer, diallylphthalate resin, unsaturated polyester resins, polyphenylene oxide, polyphenylene sulfide and polyamide.

The above-given metallic, ceramic and plastics are merely illustrative, and the present invention is not limited thereto.

According to the present invention, both thermoplastic and thermosetting resins may be used as resin adhesives. Specific examples of the resin binders include cyano acrylates, epoxy resins and polyisocyanates. However, the present invention also is not limited thereto.

The artificial tooth roots of the present invention have different optimum shapes depending on the site of application or the material type. In each of the artificial tooth roots of the following embodiments, the inner structure is comprised of a dual structure comprised of an outer root and an inner root as shown in FIGS. 3, 4 and 5.

FIG. 6 illustrates an artificial tooth root for an incisor for an upper jaw. In each of the above drawings, (a), (b), (c), (d), (e) and (f) are a front view, a left-hand side view, a right-hand side view, a back side view, a plan view and a bottom plan view, respectively.

The lateral surface of each of the artificial tooth roots is formed with axially extending alternate radial protrusions 4 and recesses 3. The foremost part of each artificial tooth root is formed with an apex 6. Each recess may be present as an opening-shaped recess 9 on pre-set sites on the lateral surface.

FIG. 7 illustrates an artificial tooth root for a cuspid and an incisor for a lower jaw. The numerals are the same as those used in FIG. 6.

FIG. 8 illustrates an artificial tooth root for a premolar for an upper jaw or a lower jaw.

FIG. 9 illustrates an example of an artificial tooth root for a molar for an upper jaw having a trifurcate tooth root section.

FIG. 10 illustrates an example of an artificial tooth root for a molar for a lower jaw having a bifurcate tooth root section.

FIG. 11 illustrates another example of an artificial tooth root for a molar for an upper jaw having a trifurcate tooth root section.

FIG. 12 illustrates still another example of an artificial tooth for a molar for a lower jaw having a tetrafurcate tooth root section.

The above-described artificial tooth root of the present invention is aimed at stress distribution and equalization by its dual structure. As compared to the conventional artificial tooth root, the artificial tooth root of the present invention is less susceptible to destruction of the ambient bone and may remain stable for a prolonged period of time. In addition, it is not insusceptible to infection and has its outer root corresponding to the alveolar bone fused satisfactorily with ambient bone resulting in facilitated formation of a bone rib affixed thereto and maintenance of the stable function for a prolonged period of time.

What is claimed is:

1. A columnar artificial tooth root, said artificial tooth root having a crown at one end and an apex at an opposite end thereof and additionally comprising an inner root member, an outer root member and a buffer material provided between the inner root member and the outer root member, said outer root member having an outer surface with axially extending protrusions and recesses formed therein and an inner surface defining an opening adapted to receive said buffer material and said inner root member and being formed from a material selected from the group consisting of metal, bioactive or bioinert ceramics evaporated or welded to metal, and a metal having a metallic or ceramic porous member, said buffer material having an outer surface in contact with and completely covering the inner surface of said outer root member and an inner surface defining an opening adapted to receive said inner root member, and said inner root member having an outer surface in contact with and completely covering the inner surface of said buffer material.

2. The artificial tooth root as claimed in claim 1 wherein the inner surface of the outer root member is cylindrically-shaped.

3. The artificial tooth root as claimed in claim 1 wherein the inner surface of the outer root member has alternating protrusions and recesses and is undulating in contour.

4. The artificial tooth root as claimed in claim 1 wherein the outer root member is formed of titanium or a titanium alloy.

5. The artificial tooth root as claimed in claim 1 wherein the bioactive ceramics is hydroxyapatite, TCP or a bioglass.

6. The artificial tooth root as claimed in claim 1 wherein the bioinert ceramics is alumina or zirconia.

7. The artificial tooth root as claimed as claim 1 wherein the inner tooth root member is formed of a material selected from the group consisting of metal, ceramics and plastics.

8. The artificial tooth root as claimed in claim 1 wherein the buffer material is a resin adhesive.

9. The artificial tooth root member as claimed in claim 8 wherein a ball-shaped stop formed of plastics is employed when charging a resin adhesive to a void space between the outer root member and the inner root.

10. The artificial tooth root as claimed in claim 1 wherein the tooth root has a round apex and may be used for any of the incisor, premolar and cuspid.

11. The artificial tooth root as claimed in claim 1 wherein the tooth root has a branched apex recessed at the center and may be employed for a molar.

\* \* \* \* \*

UNITED STATES PATENT AND TRADEMARK OFFICE
CERTIFICATE OF CORRECTION

PATENT NO. : 5 584 693
DATED : December 17, 1996
INVENTOR(S) : Katsunari NISHIHARA It is certified that error appears in the above-indentified patent and that said Letters Patent is hereby corrected as shown below:

Column 8, line 5; delete "member".

Column 8, line 8; after "root" (second occurrence) insert ---member---.

Signed and Sealed this

Twentieth Day of May, 1997

*Attest:*

BRUCE LEHMAN

*Attesting Officer*     Commissioner of Patents and Trademarks